United States Patent [19]

Byrne

[11] 4,088,444
[45] May 9, 1978

[54] PROCESS AND APPARATUS FOR STERILIZING CONTAINERS

[75] Inventor: Thomas D. Byrne, Wheeling, Ill.

[73] Assignee: Baxter Travenol Laboratories, Inc., Deerfield, Ill.

[21] Appl. No.: 694,274

[22] Filed: Jun. 9, 1976

[51] Int. Cl.² .................... A61L 1/00; A61L 3/00; A23L 3/10
[52] U.S. Cl. .......................... 21/56; 21/78; 21/96; 21/98; 99/370; 426/407; 426/412; 426/521; 426/522
[58] Field of Search ............ 21/56, 78, 94, 95, 96, 21/97, 98, 80; 426/407, 412, 521, 522; 99/370

[56] References Cited

U.S. PATENT DOCUMENTS

| 808,668 | 1/1906 | Loew | 426/407 |
|---|---|---|---|
| 2,472,970 | 6/1949 | Hanna | 99/370 |
| 3,086,837 | 4/1963 | Wilkinson et al. | 21/56 |
| 3,088,180 | 5/1963 | Lauterbach | 21/98 |
| 3,366,442 | 1/1968 | Neiss | 21/94 X |
| 3,469,988 | 9/1969 | Yawger | 426/407 |
| 3,531,300 | 9/1970 | Greenberg et al. | 21/56 X |
| 3,615,725 | 10/1971 | Van Der Winden | 21/56 X |
| 3,619,126 | 11/1971 | Carvallo | 21/56 |
| 3,661,505 | 5/1972 | Frolich | 21/56 |
| 3,704,139 | 11/1972 | Wilson | 426/407 X |
| 3,897,818 | 8/1975 | Champel | 21/94 X |
| 3,972,679 | 8/1976 | Ruig | 21/56 |
| 3,986,832 | 10/1976 | Smorenburg | 21/94 X |

FOREIGN PATENT DOCUMENTS

| 1,923,017 | 11/1969 | Germany | 21/78 |
|---|---|---|---|
| 7,105,194 | 10/1971 | Netherlands | 21/78 |

Primary Examiner—Barry S. Richman
Attorney, Agent, or Firm—Henry W. Collins; Richard G. Kinney; Eugene M. Cummings

[57] ABSTRACT

A method of sterilizing and rapidly cooling containers in a steam sterilizer by spraying the containers with a cooling fluid which has been sterilized under the same conditions as the containers.

A steam sterilizer modified with a closed loop recirculating system which provides a sterilized cooling fluid for quickly cooling the sterilized containers.

12 Claims, 7 Drawing Figures

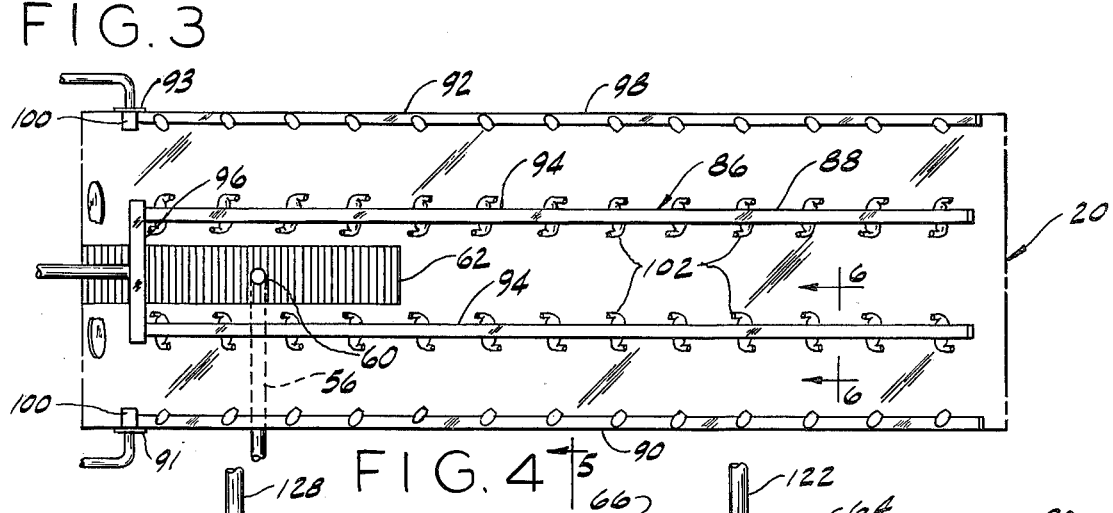
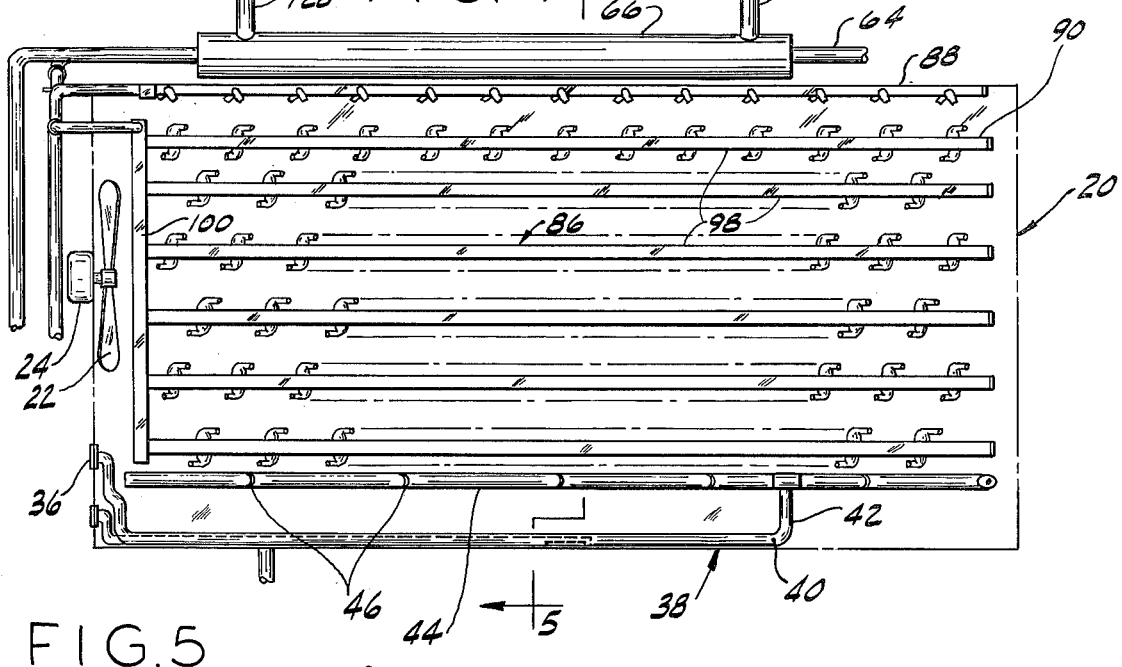
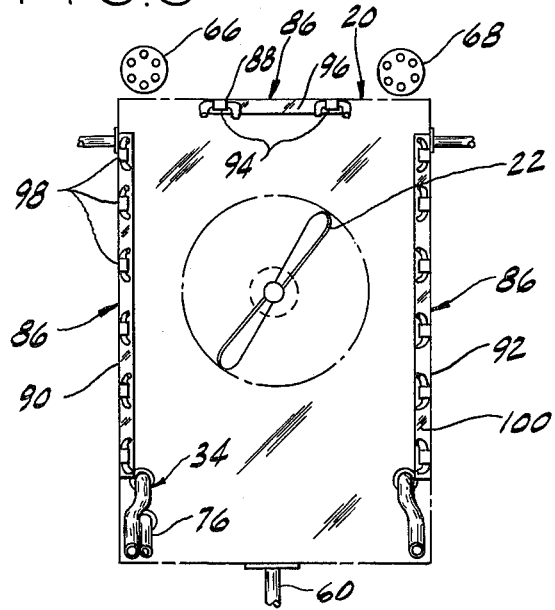
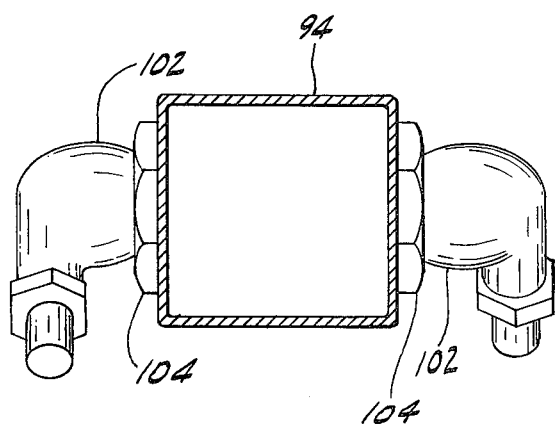

PROCESS AND APPARATUS FOR STERILIZING CONTAINERS

This invention relates to a sterile process and apparatus for rapidly cooling containers within a steam sterilizer. More particularly, this invention relates to a sterile process and apparatus for use in rapidly cooling containers such as bottles or bags filled with liquids.

When containers of fluids are sterilized, cooling is protracted and may take hours before the temperature falls to a point at which no pressure exists inside the containers. This cooling, unless otherwise provided for, can occur only by radiation from the containers and conduction through the walls of the autoclave or steam sterilizer.

Under these circumstances it has been found advantageous to cool the containers artificially. Various means have been employed, such as by pumping compressed air through the chamber. This causes a certain amount of cooling, but because of the low specific heat of air, heat is conveyed away from the containers very slowly.

Faster cooling can be achieved by spraying a liquid such as water over the containers but this method has also suffered from numerous disadvantages. These include thermal shock to the containers causing breakage when they are made from glass or the like. To reduce thermal shock and avoid breaking the containers, the temperature differential is reduced by heating the water but then the rate of cooling falls. Alternatively, a very fine spray is used at a limited rate of flow but this method similarly leads to slow cooling.

Whether the water sprayed over the containers is preheated or not, it has not been sterilized in the prior art. During cool-down pressure in the container is gradually diminished. If the seal at the cap is defective, some of the cooling water in its unsterile condition is drawn into and contaminates the contents of the containers.

In view of the above, there is a need for a process and an apparatus to quickly cool containers filled with liquids after they have been sterilized while at the same time maintaining the contents of the containers in sterile condition notwithstanding the condition of the container cap.

Among the several objects of the present invention may be noted the provision of a process and apparatus for quickly cooling liquid filled containers in a steam sterilizer while maintaining the contents of the containers in sterile condition. Other objects and features will be in part apparent and in part pointed out hereinafter.

The invention accordingly comprises the process and apparatus hereinafter described, the scope of the invention being indicated in the subjoined claims.

In the accompanying drawings, in which one of various possible embodiments of the invention is illustrated, corresponding reference characters indicate corresponding parts throughout the several views of the drawings.

FIG. 3 is a top plan view of the steam sterilizer as shown in FIG. 1;

FIG. 4 is a side elevational view of the right side of the steam sterilizer as shown in FIG. 1 in combination with FIG. 2 and additionally showing a fan;

FIG. 5 is a transverse cross-sectional view of the steam sterilizer taken along line 5—5 in FIG. 4;

FIG. 6 is an enlarged transverse cross-sectional view taken along line 6—6 in FIG. 3 of one of the pipes in the overhead spray header, showing two spray nozzles.

Figure 1:
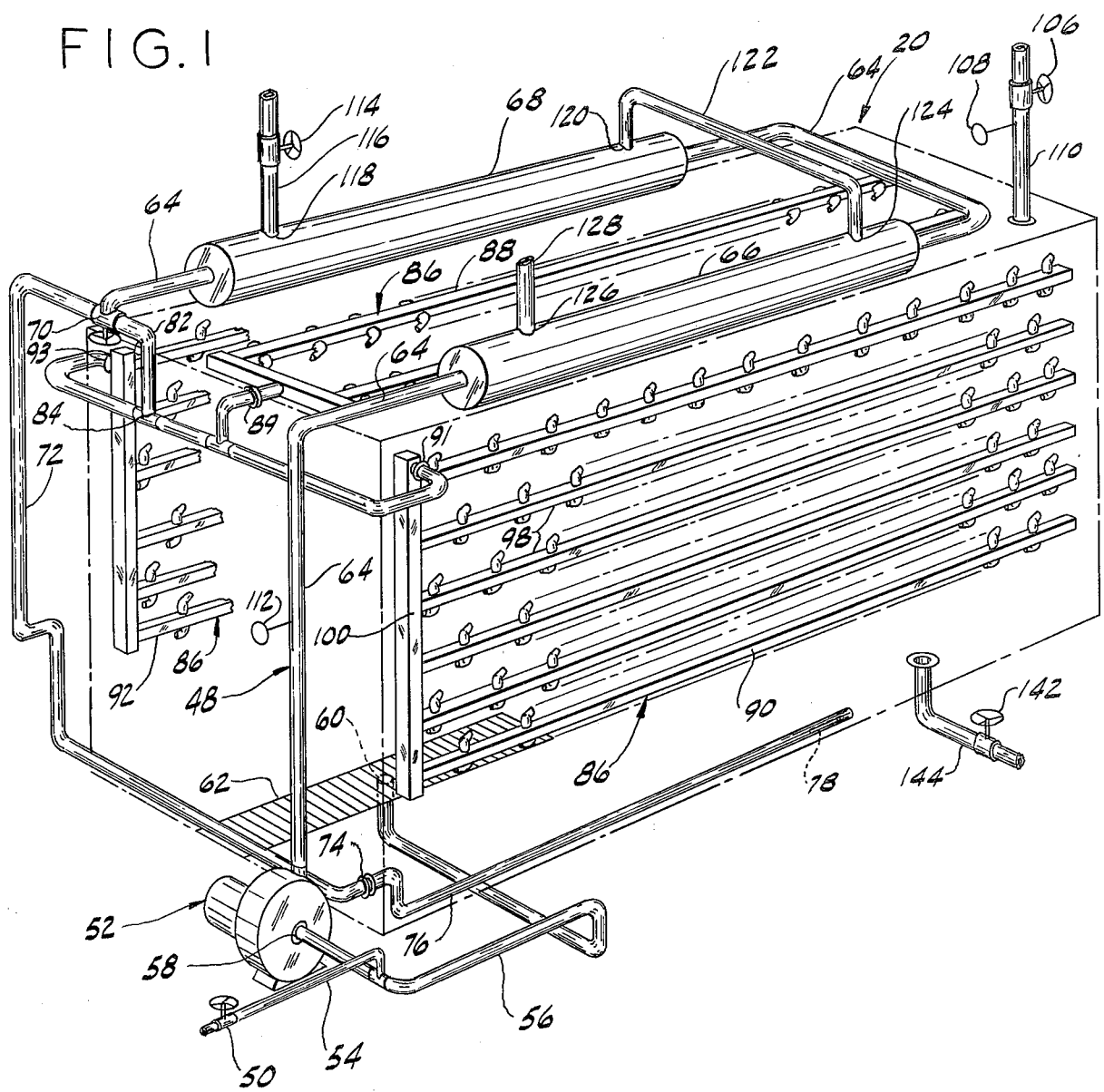
FIG. 1 is a partly schematic, perspective view of a steam sterilizer made according to the present invention but with the steam distribution system eliminated for purposes of clarity.

Referring to the drawings, the steam sterilizer of the present invention includes an autoclave chamber 20 which is shown schematically. As is customary, it is provided with a door (not shown) at one end through which filled containers, such as bottles or bags (not shown), are introduced. Once loaded, the door is closed. At the opposite end, chamber 20 is provided with a fan 22 connected to a motor 24 for rapid distribution of the steam throughout the chamber during the heating-up stage.

Figure 2:
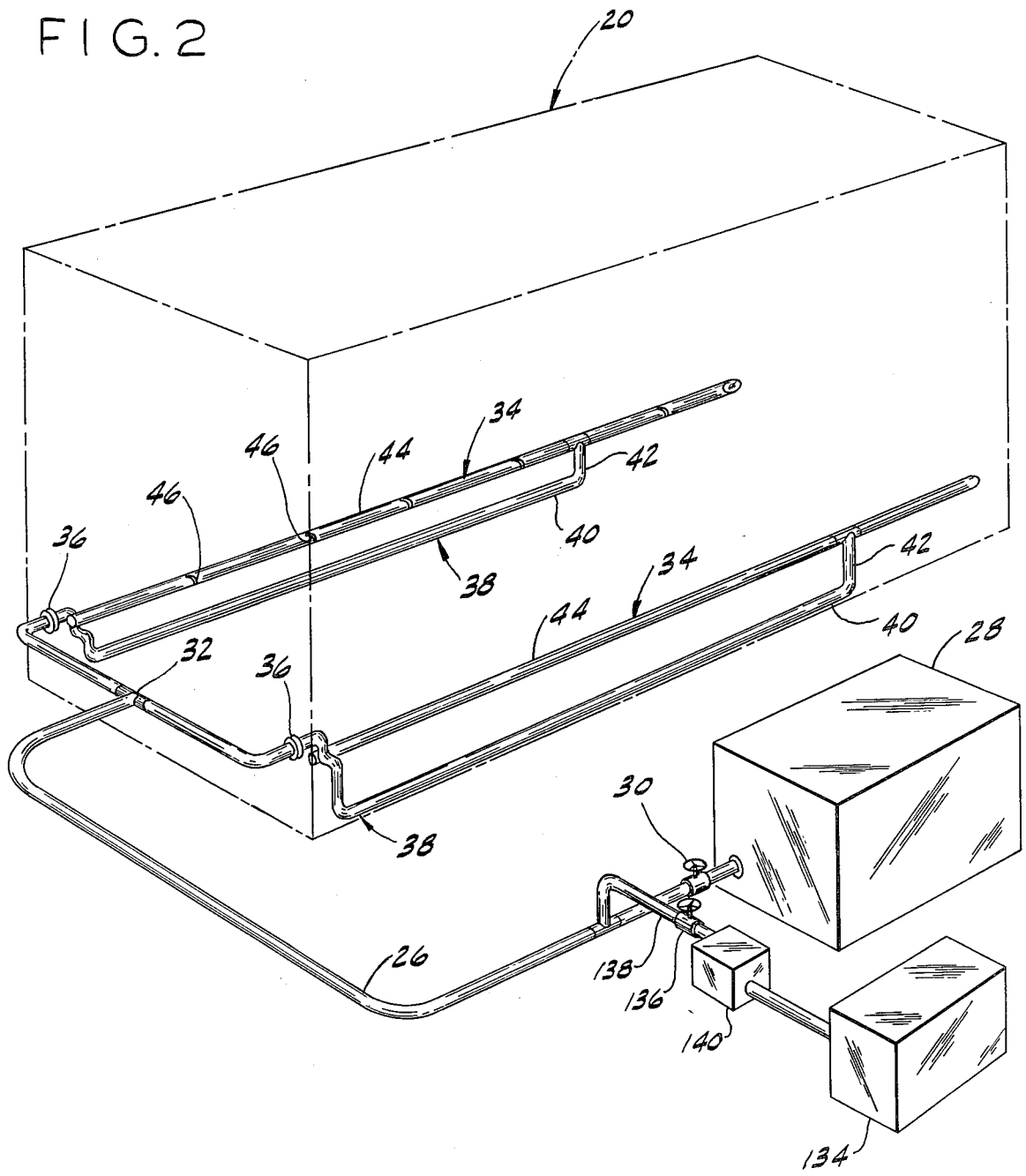
FIG. 2 is a partly schematic, perspective view of the steam distribution system for use with the sterilizer shown in FIG. 1.

As best seen in FIG. 2, steam is fed into chamber 20 through a steam inlet line 26 from a suitable boiler 28 through a shut-off valve 30. Steam inlet line 26 is connected at joint 32 to a steam distribution manifold 34. Steam distribution manifold 34 enters chamber 20 at steam inlets 36 and includes a pair of horizontally extending pipes 38, positioned adjacent the floor and on opposite sides of the chamber and extending about three-quarters the length thereof.

At ends 40, opposite steam inlets 36, pipes 38 connect with upstanding pipes 42, which in turn, connect with horizontally extending steam spreader pipes 44. Spaced along steam spreader pipes 44 are a plurality of slots 46 for admission of the steam into chamber 20. Pipes 44 extend substantially the length of the chamber and are parallel to pipes 38.

As will be described hereinafter, chamber 20 is partially filled with water before steam is admitted into the chamber. Upstanding pipes 42 are of a sufficient length so that horizontally extending steam spreader pipes 44 are maintained above the level of the water. As will be readily appreciated, the water in the bottom of chamber 20 is heated as steam passes through horizontally extending pipes 38 during heat-up of the chamber.

As mentioned above and best seen in FIG. 1 when chamber 20 has been loaded and the door closed, water is fed into a closed loop recirculating system 48 through water valve 50. The amount of water fed into the system is sufficient to prime a recirculation pump 52 and to fill the closed loop recirculating system adequate to maintain recirculation. Excess amounts of water should be avoided because the excess must be cooled, as described hereinafter, thus increasing the time necessary to cool the containers after they have been sterilized. In any case, the water level should not reach the containers and slots 46 should be above the water level.

Water valve 50 connects with a water line 54, which in turn connects with line 56 on the intake side of recirculation pump 52. One end of line 56 connects at 58 with the intake of said pump and the other end connects with a drain 60 in the bottom of chamber 20. Drain 60 includes an elongated sink (not shown) positioned midway the floor adjacent the end of chamber 20 opposite the door and, as shown, is covered with a grill 62.

The output side of pump 52 connects with line 64 which passes through first and second heat exchangers 66 and 68, respectively, and terminates at three-way valve 70. As seen in FIG. 5, heat exchangers 66 and 68 are shown as being constructed tube in shell but other exchangers with different configurations may of course be used.

In the heat-up stage, three-way valve 70 is positioned so that water flowing from line 64 passes to line 72, through recirculated water inlet 74 and into water discharge pipe 76. Discharge pipe 76 is positioned adjacent the floor and runs along one side (right side as viewed in FIG. 1) to substantially the midpoint thereof as best seen in FIG. 4.

Figure 7:
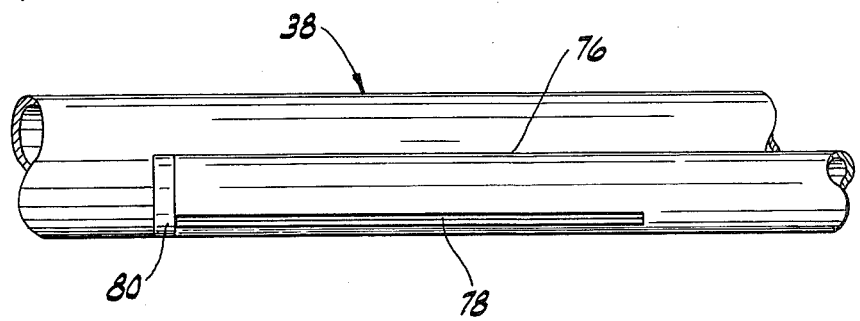
FIG. 7 is an enlarged side elevational view of the end of the water discharge pipe as shown in FIG. 4 but as viewed from the inside of the steam sterilizer.

As seen in FIG. 7, discharge pipe 76 terminates with an elongated slot 78 adjacent to an end cap 80. Slot 78 is directed towards the floor of chamber 20 but at an acute angle thereto so that water discharged from the slot is directed towards the center of the chamber.

In the cool-down stage, three-way valve 70 is positioned so that water flowing from line 64 passes to line 82 which at joint 84 connects with water spray manifold 86. As viewed in FIG. 1, water spray manifold 86 includes an overhead spray header 88 and right and left side spray headers 90 and 92, respectively. Headers 88, 90 and 92 are supplied with recirculating spray water which is admitted to chamber 20 through inlets 89, 91 and 93, respectively. Overhead spray header 88 is best seen in FIG. 3 and right side spray header is best seen in FIG. 4 as it appears from the inside of chamber 20.

Overhead spray header 88 has two lines 94 which run substantially the length of chamber 20 and which connect adjacent opposite ends and at right angles to line 96. Each of side spray headers 90 and 92 has six lines 98 which are like lines 94 and which connect at spaced intervals along and at right angles to line 100. To conserve space in chamber 20, lines 94 and 98 are constructed from tubing having a square cross-section as seen in FIG. 6.

Spaced along each of lines 94 and 98 are pairs of spray nozzles 102 mounted on opposite sides of said lines. As best seen in FIG. 6, each of nozzles 102 is pivotal at its attachment point 104 and is preferably set at about 45 degrees to the chamber wall to which the particular header is attached. For better distribution of the water sprayed from the nozzles, each pair of nozzles is oppositely directed and adjacent pairs are staggered on adjacent lines.

In use, liquid filled containers, such as bottles or bags, are stacked in successive layers on a cart and are loaded into chamber 20. The door is closed and water valve 50 opened to charge closed loop recirculating system 48 with water. Preferably, the water admitted through valve 50 is first filtered. Sufficient water is charged into the system to prime recirculation pump 52 and to provide a pool of water on the floor of chamber 20 having ample (but not excessive) volume to fill the piping adequate to maintain recirculation.

When sufficient water has been fed into the system, water valve 50 is closed, three-way valve 70 is set so that flow therethrough is to line 72, recirculation pump 52 is started and steam shut-off valve 30 is opened. At the same time, a steam vent valve 106 on chamber 20 is opened.

Steam is flowed from boiler 28 through steam inlet line 26 to steam distribution manifold 34. As it passes through horizontally extending pipes 38 it heats the water in the bottom of chamber 20 which is stirred by recirculated water sprayed from elongated slot 78 in water discharge pipe 76.

Steam mixes with and displaces air from chamber 20. When the vapors passing through vent valve 106 reach a preselected temperature as measured by temperature probe 108 in vent line 110, vent valve 106 is closed.

With vent valve 106 closed, the pressure and temperature in chamber 20 continues to rise to a preselected value. As the water in closed loop recirculating system 48 is circulated through chamber 20, it is heated and sterilized by the same conditions which sterilize the contents of the containers. For this purpose, it is preferred that the temperature of the recirculated water be monitored outside chamber 20 as in line 64 by a temperature probe 112. When this temperature reaches a preselected value, it is held at that temperature for a preselected time sufficient to obtain sterilization of the fluid filled containers and of the water in the closed loop.

When sterilization is completed, steam shut-off valve 30 is closed and three-way valve 70 is set so that flow therethrough is to line 82 and thus to water spray manifold 86. Recirculated water which has been previously sterilized along with the containers, is sprayed through nozzles 102 onto the containers. Since this water is substantially the same temperature as the containers, the containers do not undergo thermal shock or breakage.

After the containers have been sprayed with hot water, the water in closed loop recirculating system 48 is cooled at a preselected rate as it passes through heat exchangers 66 and 68. To this end, water valve 114 in water line 116 is opened and water therefrom flowed through heat exchangers 66 and 68 in counterflow relationship to the hot water in line 64. As seen in FIG. 1, cold water line 116 connects at a jacket inlet 118 near the exit of second heat exchanger 68. The cold water passing through heat exchanger 68, passes out of the exchanger at a jacket outlet 120 near the inlet of the exchanger. Water from jacket outlet 120 passes through pipe 122 to a jacket inlet 124 near the exit of first heat exchanger 66 and then out of a jacket outlet 126 near the inlet of the exchanger to a drain pipe 128.

The rate at which water is admitted through water valve 114 determines the rate at which the water in closed loop recirculating system 48 is cooled and this indirectly controls the rate at which the containers in chamber 20 are cooled. This rate, of course, should be as fast as possible without thermally shocking the containers.

When the containers are bags or the like, chamber 20 must be pressurized with air before the containers are cooled. This is not necessary when the containers are glass if care is taken to exclude most of the air during filling. But when the containers are formed from a flexible or semiflexible material, then it is necessary to exert a sufficient external pressure to counteract the gas or vapor in the package so that the container will not rupture. The amount of pressure depends upon a number of factors including the amount of force which the bags can bear without breaking.

Hence, when sterilization is completed but before hot water is sprayed from manifold 86, chamber 20 is back pressured with air from an air compressor 134. Air valve 136 is opened in an air line 138 so that air flows from air compressor 134 into steam inlet line 26. A bacterial filter 140, such as a Millipore filter, is provided in air line 138 to render the air introduced into chamber 20 sterile by filtration. As aforementioned, sufficient air pressure is applied to the chamber to keep the bags from rupturing during cooling. When this pressure has been applied, air valve 136 is closed and three-way valve 70 is set so that flow is to water spray manifold 86 and cooling is started as above described.

When the containers are glass bottles, spray manifold 86 is preferably simplified by deleting side spray headers 90 and 92. Joint 84 is therefore eliminated and the connection of line 82 is directly to inlet 89 and overhead spray header 88. Side headers 90 and 92 can be eliminated because the recirculated cooling water can effectively reach the containers if it is sprayed over the top layer and trickles down through the layers. This is because glass bottles can be racked, layer upon layer, with perforated screens therebetween. Bags, on the other hand, must be supported by racks between the layers and are ineffectively cooled if the water is only sprayed from the top. Side headers 90 and 92 are, therefore, necessary during cool-down when the containers are bags.

After the containers have been cooled for a preselected time to a preselected temperature, recirculation pump 52 is turned off and a drain valve 142 in a drain line 144 opened. Drain line 144 is connected to the floor of chamber 20 and provides a dump outlet for the water in the chamber and in closed loop recirculating system 48. To this end, chamber 20 and the piping associated with closed loop recirculating system 48 is so arranged that water is completely drained therefrom through drain line 144.

When the water has been drained from chamber 20, the door to the chamber is opened and the sterilized containers removed from the autoclave. The chamber is then ready to receive another load of containers for sterilization.

In view of the above, it will be seen that the several objects of the invention are achieved and other advantageous results attained. For example, it will be seen that the present process and apparatus provides for faster processing since less time is wasted in cooling the sterilized containers. This efficiency provides cost savings by reducing the amount of equipment needed to process a particular number of containers in a given time period.

As various changes could be made in the above process and apparatus without departing from the scope of the invention, it is intended that all matter contained in the above description or shown in the accompanying drawings shall be interpreted as illustrative and not in a limiting sense.

What is claimed is:

1. In a method for sterilizing and rapidly cooling containers in a stream sterilizer which includes loading the containers into a chamber, displacing air from the chamber by steam, heating the chamber with steam until the required sterilization temperature and pressure are reached and maintaining said sterilization conditions for a period of time sufficient to sterilize the containers, the improvement which comprises partially filling the chamber with a heat exchange liquid to form a bath of heat exchange liquid and to prime a closed loop liquid recirculation system in said sterilizer while preventing the containers from becoming immersed within said chamber bath, circulating the heat exchange liquid in said closed recirculation system during sterilization of the containers, sterilizing the heat exchange liquid in the chamber as the containers are sterilized, and subsequent to said sterilization period of time circulating the sterilized heat exchange liquid and spraying the sterilized heat exchange liquid over the sterilized containers and cooling the recirculating sterilized heat exchange liquid at a preselected rate whereby the sterilized containers are cooled with recirculated sterilized liquid and without thermal shock.

2. The method for sterilizing and rapidly cooling containers in a steam sterilizer according to claim 1 wherein the heat exchange liquid is water.

3. The method for sterilizing and rapidly cooling containers in a steam sterilizer according to claim 1 wherein the sterilized liquid is sprayed against the containers by a plurality of nozzles.

4. The method for sterilizing and rapidly cooling containers in a steam sterilizer according to claim 1 wherein said sterilized liquid is cooled by passing the sterilized liquid in the closed recirculating system through a heat exchanger, and said sterilized liquid is water.

5. The method for sterilizing and rapidly cooling containers in a steam sterilizer according to claim 4 which further includes monitoring the temperature and pressure in the chamber during cool-down and controlling the rate at which the sterilized water is cooled as it passes through the heat exchanger so that the sterilized containers sprayed therewith are cooled without thermal shock.

6. The method for sterilizing and rapidly cooling containers in a steam sterilizer according to claim 5 wherein said sterilized water is cooled by passing the sterilized water in the closed recirculating system serially through a plurality of heat exchangers having water jackets and passing cooling water through the jackets of said heat exchangers in counterflow relationship to the sterilized water passing through the heat exchangers.

7. The method for sterilizing and rapidly cooling containers in a steam sterilizer according to claim 6 wherein said containers are flexible and which further includes pressuring the chamber with sterile air after the containers and circulated water are sterilized and before the sterilized water is sprayed on said containers, said chamber being pressurized to the pressure necessary to prevent rupture of the flexible containers during cool-down.

8. In a steam sterilizer for sterilizing and rapidly cooling containers, said sterilizer including an enclosed chamber including an access door at one end thereof through which containers to be sterilized may be brought into and moved out of said chamber, means for providing controlled entry and exit of air from said chamber, a steam piping means positioned in said chamber, a plurality of apertures arranged in spaced relation therealong for spraying steam from said pipe to a void space in said chamber in which containers to be sterilized may be positioned, an elongate water spray header positioned in said chamber, said header including a plurality of spray nozzles positioned in spaced relation therealong, and a drain at the bottom of said chamber for removing liquid therefrom, the improvement which comprises a recirculation system adapted to move a quantity of sterilized water in a closed loop through the sterilizer during operation thereof, said closed loop having a heat-up loop and a cool-down loop, said closed loop including a bath of heat exchange liquid within the enclosed chamber, said bath being within both said heat-up loop and said cool-down loop and being of a depth such that containers are not immersed therewithin while positioned within said void space or during their movement into or out of said chamber, said heat-up loop including means for circulating water that is sterilized through the operation of said steam piping means, said cool-down loop including means for recirculating said sterilized water and for spraying said sterilized water from said header to said void space and to containers therewithin, and said cool-down loop including means for eliminating thermal shock to said containers during cool-down thereof after sterilization.

9. The steam sterilizer for sterilizing and rapidly cooling containers in a sterilization chamber according to claim 8 wherein the recirculation system includes a pump for circulating the sterilized water.

10. The steam sterilizer for sterilizing and rapidly cooling containers in a sterilization chamber according to claim 9 wherein the recirculation system includes a heat exchanger for cooling the sterilized water.

11. The steam sterilizer for sterilizing and rapidly cooling containers in a sterilization chamber according to claim 10 wherein said means for eliminating thermal shock includes a control means for selectively cooling the sterilized water in the chamber during sterilization of the containers as it passes through the heat exchanger at a rate which avoids thermal shock to the containers.

12. The steam sterilizer for sterilizing and rapidly cooling containers in a sterilization chamber according to claim 11 wherein there is more than one heat exchanger, each of which has a water jacket for cooling water, means for flowing the cooling water through said heat exchangers in counterflow relationship to the sterilized water circulating in the recirculation system.

* * * * *